United States Patent [19]

Schach et al.

[11] Patent Number: 5,502,260
[45] Date of Patent: * Mar. 26, 1996

[54] PROCESS FOR PREPARING MULTIPLY FLUORINATED NITROBENZENES

[75] Inventors: Thomas Schach, Gernsheim; Theodor Papenfuhs, Frankfurt am Main, both of Germany

[73] Assignee: Hoechst Aktiengesellschaft, Frankfurt, Germany

[ * ] Notice: The portion of the term of this patent subsequent to Dec. 19, 2012, has been disclaimed.

[21] Appl. No.: 276,951

[22] Filed: Jul. 19, 1994

[30] Foreign Application Priority Data

Jul. 21, 1993 [DE] Germany ............... 43 24 365.7

[51] Int. Cl.$^6$ ............... C07C 201/2
[52] U.S. Cl. ............... 568/938; 570/127; 570/141; 570/170
[58] Field of Search ............... 570/127, 141, 570/147, 170; 568/938

[56] References Cited

U.S. PATENT DOCUMENTS

| | | | |
|---|---|---|---|
| 3,064,058 | 11/1962 | Duesel | 568/937 |
| 3,453,337 | 7/1969 | Bennett et al. | 570/147 |
| 4,140,719 | 2/1979 | Tull et al. | 564/417 |
| 4,164,517 | 8/1979 | Fuller | 568/938 |
| 4,229,365 | 10/1980 | Oeser et al. | 568/938 X |
| 4,287,374 | 9/1981 | North | 568/937 |
| 4,418,229 | 11/1983 | White | 568/938 X |
| 4,684,734 | 8/1987 | Kaieda et al. | 546/345 |
| 4,937,397 | 6/1990 | Pews et al. | 570/147 |
| 5,081,288 | 1/1992 | Blank et al. | 570/147 X |
| 5,294,742 | 3/1994 | Schach et al. | 568/938 |
| 5,315,043 | 5/1994 | Fernandez et al. | 568/932 |
| 5,349,098 | 9/1994 | Kumai et al. | 570/141 |

FOREIGN PATENT DOCUMENTS

WO87/04149   7/1987   WIPO .

Primary Examiner—Richard D. Lovering
Assistant Examiner—Valerie Fee
Attorney, Agent, or Firm—Connolly & Hutz

[57] ABSTRACT

Multiply, preferably doubly or triply, fluorinated nitrobenzenes are prepared in an advantageous way from the corresponding chloronitrobenzenes and an alkali metal fluoride in a chlorine-fluorine exchange reaction by catalyzing the reaction with a quaternary ammonium compound comprising at least one alkoxypolyoxyalkyl radical.

10 Claims, No Drawings

PROCESS FOR PREPARING MULTIPLY FLUORINATED NITROBENZENES

The present invention relates to an improved process for preparing multiply fluorinated nitrobenzenes by reaction of the corresponding chloronitrobenzenes with alkali metal fluorides in the presence of a novel catalyst system.

Halogen exchange, preferably that of activated chloronitrobenzenes or bromonitrobenzenes, is a customary method for introducing fluoro substituents into an aromatic system. In general, the reaction is carried out in the presence of aprotic dipolar solvents and alkali metal fluorides as fluoride source (U.S. Pat. No. 3,064,058). Prominent disadvantages of these processes are the high reaction temperatures, moderate product yields and long reaction times.

As alternatives, use can be made of conventional phase transfer catalysts which allow some of the above-described disadvantages to be improved. Other problems, such as, for example, poor stirrability of the reaction suspension in solvent-free processes, remain. The phase transfer catalysts hitherto used have been quaternary alkylammonium or alkylphosphonium salts (U.S. Pat. No. 4,287,374), pyridinium salts (WO 87/04149) or crown ethers which, in part, show only low reactivities or are only moderately stable at the reaction temperatures required.

Multiple chlorine-fluorine exchange reactions without solvent have hitherto been possible only to a limited extent. The high salt content of the reaction suspension generally led to non-stirrable systems which lead to only small conversions and yields, even under the most favorable conditions. A double Cl/F exchange was hitherto successful only in the presence of suitable solvents such as, for example, sulfolane or dimethyl sulfoxide (U.S. Pat. No. 4,164,517, DE-A 3 642 332).

In view of these limitations and disadvantages there was a great need for an improved process by which means the disadvantages inherent in the known processes are avoided and good to very good yields, lower reaction temperatures and shortened reaction times are made possible and small amounts of polymeric decomposition products are obtained. Particular importance has been attached to, in particular, coping with stirring problems and work-up problems in solvent-free processes and in processes using only very small amounts of solvent.

It has been found that nitrobenzenes can be multiply fluorinated in an advantageous way by reacting the corresponding chloronitrobenzenes with alkali metal fluorides in the presence of a quaternary ammonium compound comprising at least one alkoxypolyoxyalkyl radical.

The present invention provides a process for preparing multiply fluorinated nitrobenzenes by reaction of a compound of the formula (4)

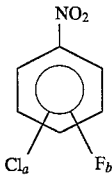
(4)

in which
a is a number from 2 to 4 and
b is a number from 0 to 2,
with an alkali metal fluoride in the presence of a catalyst, wherein the catalyst consists essentially of
a) one or more quaternary ammonium compound(s) of the formula (1)

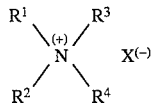
(1)

in which
$R^1$, $R^2$ and $R^3$ are identical or different and are a linear or branched alkoxypolyoxyalkyl radical of the formula $-(C_mH_{2m}O)_pR^5$, in which $R^5$ is hydrogen or a linear or branched alkyl radical having from 1 to 16, preferably from 1 to 8, carbon atoms, m is an integer from 1 to 10, preferably from 1 to 5, and p is a number from 1 to 15, preferably from 2 to 10; or a linear or branched alkyl radical having from 1 to 30, preferably from 1 to 18, carbon atoms; or an unsubstituted phenyl or naphthyl radical; or a substituted phenyl or naphthyl radical, with the substituents being halogen, $C_1$–$C_4$-alkyl, $C_1$–$C_4$-alkoxy, nitro or cyano;
$R^4$ is a linear or branched alkoxypolyoxyalkyl radical of the formula $-(C_mH_{2m}O)_pR^5$; and
$X^e$ is an inorganic anion, preferably fluoride, chloride, bromide, $SO_4^{2-}/2$ or hydrogen sulfate;
or of a mixture of the component a) and
b) one or more quaternary ammonium salt(s) or phosphonium salt(s) of the formula (2)

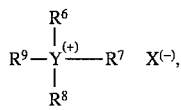
(2)

in which
$R^6$, $R^7$, $R^8$ and $R^9$ are identical or different and are a linear or branched alkyl radical having from 1 to 22, preferably from 1 to 16, carbon atoms; or an unsubstituted or substituted aryl radical or a $C_1$–$C_4$-alkyl-aryl radical, with aryl being phenyl or naphthyl and said substituents being halogen, $C_1$–$C_4$-alkyl, $C_1$–$C_4$-alkoxy, nitro or cyano; and
Y is N or P;
or of a mixture of the component a) and
c) one or more polyether(s) of the formula (3)

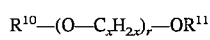
(3), in which
$R^{10}$ and $R^{11}$ are identical or different and are hydrogen or a linear or branched alkyl radical having from 1 to 16, preferably from 1 to 8, carbon atoms,
x is an integer from 2 to 6, preferably 2 or 3, and
r is a number from 0 to 20, preferably from 4 to 14;
or a crown ether;
or of a mixture of the components a), b) and c).

The catalyst preferably consists exclusively of component a), but it can be advantageous to use a mixture of the components a) and b) or of the components a) and c) or of the components a), b) and c).

The mixing ratios of the components a) and b), a) and c) and also a), b) and c) can vary within a wide range, with the proviso that the component a) makes up at least 5% by weight, preferably from 20 to 80% by weight of the total catalyst.

In the linear or branched alkoxypolyoxyalkyl radical of the formula $-(C_mH_{2m}O)_pR^5$ present in the compound of the formula (1), identical or different alkoxy units can be linked to one another.

The number of linear or branched alkoxypolyoxyalkyl radicals present in the compound of the formula (1) is preferably 1 or 2. For the purposes of the present invention, particularly preferred compounds of the formula (1) are dimethyldi(ethoxypolyoxypropyl)ammonium chloride, dimethyldi(ethoxypolyoxypropyl methyl ether)ammonium chloride, dimethyl(ethoxypolyoxypropyl)(ethoxypolyoxypropyl methyl ether)ammonium chloride, dimethyldi(ethoxypolyoxyethyl)ammonium chloride, dimethyldi(ethoxypolyoxyethyl methyl ether)ammonium chloride, dimethyl(ethoxypolyoxyethyl)(ethoxypolyoxyethyl methyl ether)ammonium chloride, each having a mean chain length p of 3, furthermore trimethyl(ethoxypolyoxypropyl)ammonium chloride and trimethyl(ethoxypolyoxypropyl methyl ether)ammonium chloride, each having a mean chain length p of 8, or a mixture of the specified compounds.

The described compounds of the formula (1) can be prepared in a known way (U.S. Pat. No. 3,123,641; U.S. Pat. No. 3,141,905) from corresponding ethanolamines which, after reaction with alkylene oxides and subsequent quaternization with or without simultaneous etherification, give the desired compounds in good yields.

For the purposes of the present invention, preferred compounds of the formula (2) are octadecyltrimethylammonium chloride, distearyldimethylammonium chloride, tetramethylammonium chloride, tetramethylammonium bromide, hexadecyltrimethylammonium chloride, benzyltrimethylammonium chloride, hexadecyltributylphosphonium bromide, stearyltributylphosphonium bromide, tetrabutylphosphonium chloride, tetrabutylphosphonium bromide and tetraoctylphosphonium bromide.

For the purposes of the present invention, preferred polyethers of the formula (3) possess a mean molecular mass between 300 and 800. Particular preference is given to a mixture of polyethylene glycol dimethyl ethers having chain lengths r of from 6 to 17 and a mean molecular mass of 500. In place of or in combination with polyethers of the formula (3), customary crown ethers, for example 18-crown-6, can also be used.

Suitable starting compounds of the formula (4) for the process of the invention are: Dichloronitrobenzenes such as, for example, 2,4-dichloronitrobenzene, 2,4-dichloro-3-fluoronitrobenzene and 2,4-dichloro-5-fluoronitrobenzene; trichloronitrobenzenes such as, for example, 2,4,5-trichloronitrobenzene, 2,3,4-trichloronitrobenzene, 2,3,4-trichloro-5-fluoronitrobenzene and 2,4,5-trichloro-3-fluoronitrobenzene.

By means of the process of the invention, two or three, preferably two, chlorine atoms in the specified starting compounds can be replaced by fluorine atoms, so that the end products obtained are, for example: Difluoronitrobenzenes such as, for example, 2,4-difluoronitrobenzene, 5-chloro-2,4-difluoronitrobenzene and 3-chloro-2,4-difluoronitrobenzene; trifluoronitrobenzenes such as, for example, 2,3,4-trifluoronitrobenzene, 2,4,5-trifluoronitrobenzene, 3-chloro-2,4,5-trifluoronitrobenzene and 5-chloro-2,3,4-trifluoronitrobenzene.

The alkali metal fluorides used are preferably potassium fluoride, rubidium fluoride or cesium fluoride or combinations of these, in particular potassium fluoride. It is an advantage of the process of the invention that the alkali metal fluorides used can have a water content of up to 3%. This makes it possible, for example, to use technical grade potassium fluoride without pretreatment.

In the process of the invention, the catalyst is advantageously used in amounts of from 1 to 35% by weight, preferably from 5 to 15% by weight, based on the aromatic starting compound. The molar ratio of catalyst to starting compound is here equal to or less than 1:10, preferably from 1:15 to 1:50.

As regards the molar ratio of the alkali metal fluoride to the starting compound, from 60 to 200 mol %, preferably from 100 to 140 mol %, based on each chlorine atom to be replaced, of alkali metal fluoride are advantageously used.

Double or triple chlorine-fluorine exchange reactions for preparing fluoronitrobenzenes have hitherto only been possible in the presence of solvents. The high salt content of the reaction suspension generally led to non-stirrable systems which led to only small conversions and yields, even under the most favorable conditions. In the process of the invention there are now, even at very high salt contents in the reaction suspension, no stirring problems so that even double or triple exchange reactions can usually be carried out without problems in the absence of solvent. Finally, the simultaneously significantly lower reaction temperatures in comparison with the prior art lead, together with the good stirrability of the reaction suspension, to a significant increase in the yield and a reduction in secondary reactions.

While temperatures of from 200° C. to over 300° C. have hitherto been required for chlorine-fluorine exchange reactions, the reaction temperatures of the process of the invention are from 80° to 220° C., preferably from 90° to 180° C., in particular from 120° to 170° C.

The process of the invention can be carried out in the presence or absence of solvents. If solvents are used, aprotic and dipolar aprotic and also protic solvents are suitable. Suitable dipolar aprotic solvents are, for example, dimethyl sulfoxide, dimethyl sulfone, sulfolane, dimethylformamide, dimethylacetamide, 1,3-dimethylimidazolin-2-one, acetonitrile and benzonitrile. Suitable aprotic solvents without pronounced dipolar character are, for example, benzene, toluene, xylene, chlorotoluenes, chlorobenzene and dichlorobenzenes. The use of protic solvents such as, for example, alcohols is likewise possible. Protic solvents used are methanol, ethanol, propanol, butanol, i-propanol or polyalkylene glycols having ethylene, propylene or butylene units.

The aprotic or dipolar aprotic solvent can be used in any amount, however preference is given to using small amounts in the range from 5 to 30% by weight, based on the aromatic used. When using protic solvents, the amounts used are in the range from 0.1 to 5% by weight, preferably from 0.1 to 2% by weight, based on the aromatic used.

The catalyst of the invention can be used at atmospheric pressure and also at superatmospheric or subatmospheric pressure. These properties are utilized, for example, by adding small amounts of a low-boiling aprotic solvent which forms an azeotrope with water, such as, for example, benzene, xylene, mesitylene or toluene, to the reaction suspension prior to the start of the reaction. Subsequently, a part of the solvent is again removed together with water from the reaction suspension by application of a vacuum. This process procedure allows the reaction rate and the yield to be increased and the formation of by-products to be minimized.

The process of the invention can be carried out in the presence or absence of atmospheric oxygen; preference is given to working under protective gas such as, for example, argon or nitrogen. In the process of the invention it must be ensured that the reaction mixture is well mixed during the whole reaction.

Fluoronitrobenzenes play an important role as intermediates in the field of crop protection and as synthetic building blocks for pharmaceuticals and dyes.

The following examples illustrate the process of the invention, without limiting it to them. For the purposes of the present invention, "polyethylene glycol dimethyl ether 500" is the said polyether having a mean molecular mass of about 500.

The trimethyl(ethoxypolyoxypropyl)ammoniumchloride used in the examples has a mean chain length p of 8 and was used as a product having a purity of from 84 to 89% by weight. This product additionally contains from 10 to 13% by weight of free polypropylene glycol and up to 2% by weight of water.

The dimethyldi(ethoxypolyoxypropyl)ammonium chloride used has a mean chain length p of 3 and is a product having a purity of from 90 to 95% by weight, which additionally contains from 5 to 10% by weight of polypropylene glycol and about 0.2% by weight of water.

If the two catalysts were used as etherified compounds, the polypropylene glycols were likewise in etherified form. In the case of dimethoxydi(ethoxypolyoxypropyl methyl ether)ammonium chloride, the degree of etherification was 86%.

The course of the reaction over time was followed by gas chromatographic analysis (GC) and the amount of the desired product present in each case in the reaction mixture was given in the form of GC percentage areas.

EXAMPLE 1

2,4-Difluoronitrobenzene

In a 2.5 liter flange flask fitted with a distillation bridge and anchor stirrer, 511 g (8.8 mol) of potassium fluoride, 89.9 g (0.17 mol) of dimethyldi(ethoxypolyoxypropyl)ammonium chloride and 44.5 g (0.09 mol) of polyethylene glycol dimethyl ether 500 were introduced at 100° C. into the melt of 768 g (4 mol) of 2,4-dichloronitrobenzene. Subsequently, 50 g (0.47 mol) of xylene were added and the reaction suspension was azeotropically dried by application of a vacuum of 20 mbar and heating to 130° C. After the xylene had been distilled off, the distillation bridge was replaced by a reflux condenser, the reaction suspension was heated to 140° C. and stirred for 21 hours at this temperature. Subsequently, the reaction suspension was cooled to 70° C. and filtered with suction (70° C.). The salts separated off were washed twice with a total of 180 g of xylene and the combined organic phases were fractionated. 535 g (84% of theory) of 2,4-difluoronitrobenzene were isolated. Amount of 2,4-difluoronitrobenzene formed, according to GC analysis: after 6 hours, 57 GC area-%; after 21 hours, 86 GC area-%.

EXAMPLE 2

2,4-Difluoronitrobenzene

In a 2.5 liter flange flask fitted with a distillation bridge and anchor stirrer, 511 g (8.8 mol) of potassium fluoride and 40 g (0.07 mol) of dimethyldi(ethoxypolyoxypropyl)ammonium chloride, 30.0 g (0.06 mol) of polyethylene glycol dimethyl ether 500 and 11.9 g (0.035 mol) of tetrabutylphosphoniumbromide were introduced at 100° C. into the melt of 768 g (4 mol) of 2,4-dichloronitrobenzene. Subsequently, 80 g (0.75 mol) of xylene were added and the reaction suspension was azeotropically dried by application of a vacuum of 30 mbar and heating to 130° C. After the xylene had been distilled off, the distillation bridge was replaced by a reflux condenser, the reaction suspension was heated to 140° C. and stirred for 21 hours at this temperature. Subsequently, the reaction suspension was cooled to 70° C. and filtered with suction (70° C.). The salts separated off were washed twice with a total of 180 g of xylene and the combined organic phases were fractionated. 553 g (87% of theory) of 2,4-difluoronitrobenzene were isolated. Amount of 2,4-difluoronitrobenzene formed, according to GC analysis: after 5 hours, 23 GC area-%; after 21 hours, 89 GC area-%.

EXAMPLE 3

2,4-Difluoronitrobenzene

In a 500 ml flange flask fitted with a distillation bridge and impeller stirrer, 72.0 g (1.24 mol) of potassium fluoride, 14.0 g (0.02 mol) of dimethyldi(ethoxypolyoxypropyl)ammonium chloride and 7.0 g (0.013 mol) of polyethylene glycol dimethyl ether 500 were introduced at 100° C. into the melt of 120 g (0.62 mol) of 2,4-dichloronitrobenzene. The temperature was raised to 120° C. and the reaction suspension was stirred for 28 hours at this temperature. Amount of 2,4-difluoronitrobenzene formed: after 6 hours, 11 GC area-%; after 28 hours, 56 GC area-%.

EXAMPLE 4

2,3,4-Trifluoronitrobenzene

In a 2.5 liter flange flask fitted with a distillation bridge and anchor stirrer, 581 g (10.0 mol) of potassium fluoride, 71.1 g (0.1 mol) of trimethyl (ethoxypolyoxypropyl)ammonium chloride, 20.0 g (0.04 mol) of polyethylene glycol dimethyl ether 500 and 13.6 g (0.04 mol) of tetrabutylphosphoniumbromide were introduced at 110° C. into the melt of 840 g (4 mol) of 2,4-dichloro-3-fluoronitrobenzene. Subsequently, 80 g (0.75 mol) of xylene were added and the reaction suspension was azeotropically dried by application of a vacuum of 30 mbar and heating to 120° C. After the xylene had been distilled off, the distillation bridge was replaced by a reflux condenser, the reaction suspension was heated to 130° C. and stirred well for 21 hours at this temperature. Subsequently, the reaction suspension was cooled to 25° C. and filtered with suction (25° C.). The salts separated off were washed twice with a total of 180 g of xylene and the combined organic phases were fractionated. 506 g (72% of theory) of 2,3,4-trifluoronitrobenzene were isolated. Amount of 2,3,4-trifluoronitrobenzene formed, according to GC analysis: after 5 hours, 15 GC area-%; after 21 hours, 74 GC area-%.

EXAMPLE 5

5-Chloro-2,4-difluoronitrobenzene

In a 2.5 liter flange flask fitted with a distillation bridge and anchor stirrer, 523 g (9.0 mol) of potassium fluoride and 85.3 g (0.12 mol) of trimethyl(ethoxypolyoxypropyl)ammonium chloride and 19.3 g (0.06 mol) of tetrabutylphosphonium bromide were introduced at 100° C. into the melt of 905 g (4 mol) of 2,4,5-trichloronitrobenzene. Subsequently, 80 g (0.75 mol) of xylene were added and the reaction suspension was azeotropically dried by application of a vacuum of 40 mbar and heating to 120° C. After the xylene had been distilled off, the distillation bridge was replaced by a reflux condenser, the reaction suspension was heated to 130° C. and stirred for 21 hours at this temperature. Subsequently, the reaction suspension was cooled to 25° C. and filtered with suction (25° C.). The salts separated off were washed twice with a total of 180 g of xylene and the combined organic phases were fractionated. 619 g (80% of theory) of 5-chloro-2,4-difluoronitrobenzene were isolated. Amount of 5-chloro-2,4-difluoronitrobenzene formed, according to GC analysis: after 5 hours, 38 GC area-%; after 21 hours, 89 GC area-%.

EXAMPLE 6

2,4,5-Trifluoronitrobenzene

In a 2.5 liter flange flask fitted with a distillation bridge and anchor stirrer, 581 g (10.0 mol) of potassium fluoride, 71.1 g (0.1 mol) of trimethyl(ethoxypolyoxypropyl)ammonium chloride, 20.0 g (0.04 mol) of polyethylene glycol dimethyl ether 500 and 13.6 g (0.04 mol) of tetrabutylphosphoniumbromide were introduced at 110° C. into the melt of 840 g (4 mol) of 2,4-dichloro-5-fluoronitrobenzene. Subsequently, 80 g (0.75 mol) of xylene were added and the reaction suspension was azeotropically dried by application of a vacuum of 30 mbar and heating to 120° C. After the xylene had been distilled off, the distillation bridge was replaced by a reflux condenser, the reaction suspension was heated to 130° C. and stirred for 21 hours at this temperature. Subsequently, the reaction suspension was cooled to 25° C. and filtered with suction (25° C.). The salts separated off were washed twice with a total of 180 g of xylene and the combined organic phases were fractionated. 506 g (72% of theory) of 2,4,5-trifluoronitrobenzene were isolated. Amount of 2,4,5-trifluoronitrobenzene formed, according to GC analysis: after 5 hours, 15 GC area-%; after 21 hours, 74 GC area-%.

EXAMPLE 7

2,3,4-Trifluoronitrobenzene

In a 2.5 liter flange flask fitted with a distillation bridge and anchor stirrer, 488 g (8.4 mol) of potassium fluoride, 40.0 g (0.06 mol) of trimethyl(ethoxypolyoxypropyl methyl ether)ammonium chloride, 20.0 g (0.04 mol) of polyethylene glycol dimethyl ether 500 and 20.4 g (0.06 mol) of tetrabutylphosphonium bromide were introduced at 110° C. into the melt of 840 g (4 mol) of 2,4-dichloro-3-fluoronitrobenzene. Subsequently, 60 g (0.57 mol) of xylene were added and the reaction suspension was azeotropically dried by application of a vacuum of 30 mbar and heating to 130° C. After the xylene had been distilled off, the distillation bridge was replaced by a reflux condenser, the reaction suspension was heated to 150° C. and stirred for 21 hours at this temperature. Subsequently, the reaction suspension was cooled to 25° C. and filtered with suction (25° C.). The salts separated off were washed twice with a total of 400 g of xylene and the combined organic phases were fractionated. 516.8 g (73% of theory) of 2,3,4-trifluoronitrobenzene were isolated. Amount of 2,3,4-trifluoronitrobenzene formed, according to GC analysis: after 5 hours, 14 GC area-%; after 21 hours, 75 GC area-%.

EXAMPLE 8

2,3,4-Trifluoronitrobenzene

In a 1.5 liter flange flask fitted with a distillation bridge and anchor stirrer, 488 g (8.4 mol) of potassium fluoride and 40.0 g (0.07 mol) of dimethyldi(ethoxypolyoxypropyl methyl ether)ammonium chloride, 20.0 g (0.04 mol) of polyethylene glycol dimethyl ether 500 and 20.4 g (0.06 mol) of tetrabutylphosphonium bromide were introduced at 110° C. into the melt of 840 g (4 mol) of 2,4-dichloro-3-fluoronitrobenzene. Subsequently, the mixture was azeotropically dried using 60 g (0.57 mol) of xylene and stirred for 21 hours at a temperature of 150° C. Amount of 2,3,4-trifluorobenzene formed: after 5 hours, 13 GC area-%; after 21 hours, 65 GC area-%.

COMPARATIVE EXAMPLE

2,4-Difluoronitrobenzene

In a 2 liter flange flask fitted with a distillation bridge and stirrer, 36 g (0.33 mol) of tetramethylammonium chloride, 72 g (0.15 mol) of polyethylene glycol dimethyl ether 500 and 1044 g (18 mol) of potassium fluoride were introduced at 140° C. into the melt of 1440 g (7.5 mol) of 2,4-dichloronitrobenzene. Subsequently, 108 g (1.02 mol) of xylene were added and the reaction suspension was azeotropically dried by application of a vacuum of 45 mbar and heating to 160° C. After the xylene had been distilled off, the distillation bridge was replaced by a reflux condenser, the reaction suspension was heated to 200° C. and stirred for 8 hours at this temperature. 177 g (15% of theory) of 2,4-difluoronitrobenzene and 1029 g of 2,4-dichloronitrobenzene and by-products were isolated. Amount of 2,4-difluoronitrobenzene formed, according to GC analysis: after 3 hours, 8 GC area-%; after 8 hours, 17 GC area-%.

EXAMPLE 9

2,4-Difluoronitrobenzene a) Initial batch

In a 1.5 liter flange flask fitted with an anchor stirrer and distillation bridge, 60 g (0.11 mol) of dimethyldi(ethoxypolyoxypropyl methyl ether)ammonium chloride, 10 g (0.02 mol) of polyethylene glycol dimethyl ether 500 and 465 g (8 mol) of potassium fluoride were introduced in portions at 70° C. into the melt of 768 g (4.0 mol) of 2,4-dichloronitrobenzene. Subsequently, the reaction suspension was admixed with 30 g of xylene, heated to 120° C. and azeotropically dried under reduced pressure. The reaction temperature was then increased to 180° C. and the mixture was stirred for 12 hours at this temperature. Subsequently, the mixture was cooled to 70° C., admixed with 100 g of xylene and the inorganic salts formed were filtered off. The amount of 2,4-difluoronitrobenzene isolated was, after fractionation, 370.5 g (58.1% of theory), besides 220 g of intermediate products and 2,4-dichloronitrobenzene.

b) Subsequent batch

The 220 g of intermediate products and 2,4-dichloronitrobenzene from Example 9a) were admixed with 548.0 g (2.85 mol) of fresh 2,4-dichloronitrobenzene, and the reaction was carried out as for the initial batch. The amount of 2,4-difluoronitrobenzene isolated was, after fractionation, 420.2 g (92.7% of theory), based on fresh 2,4-dichloronitrobenzene used, besides 160 g of intermediate products and 2,4-dichloronitrobenzene.

EXAMPLE 10

2,3,4-Trifluoronitrobenzene a) Initial batch

In a 1.5 liter flange flask fitted with an anchor stirrer and distillation bridge, 54.9 g (0.1 mol) of dimethyldi(ethoxypolyoxypropyl methyl ether)ammonium chloride, 30 g (0.02 mol) of polyethylene glycol dimethyl ether 500 and 488 g (8.4 mol) of potassium fluoride were introduced in portions at 70° C. into the melt of 850 g (4.0 mol) of 2,4-dichloro-3-fluoronitrobenzene. Subsequently, the reaction suspension was admixed with 30 g of xylene, heated to 110° C. and azeotropically dried under reduced pressure. The reaction temperature was then increased to 150° C. and the mixture was stirred for 12 hours at this temperature. Subsequently, the mixture was cooled to 70° C., admixed with 100 g of xylene and the inorganic salts formed were filtered off. The amount of 2,3,4-trifluoronitrobenzene isolated was, after fractionation, 439 g (62.0% of theory), besides 145 g of intermediate products and 2,4-dichloro-3-fluoronitrobenzene.

b) Subsequent batch

The 145 g of intermediate products and 2,4-dichloro-3-fluoronitrobenzene from Example 10a) were admixed with 695.0 g (3.30 mol) of fresh 2,4-dichloro-3-fluoronitrobenzene and the reaction was carried out as for the initial batch. The amount of 2,3,4-trifluoronitrobenzene isolated was, after fractionation, 415.2 g (76.9% of theory), based on fresh 2,4-dichloro-3-fluoronitrobenzene used, besides 170 g of intermediate products and 2,4-dichloro-3-fluoronitrobenzene.

We claim:

1. A process for preparing multiply fluorinated nitrobenzenes comprising the step of reacting a compound of the formula (4)

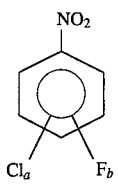

in which a is a number from 2 to 4 and b is a number from 0 to 2; with an alkali metal fluoride, in the presence of a catalyst, wherein the catalyst consists essentially of:

a component a) which consists essentially of one quaternary ammonium compound corresponding to formula 1 or a plurality of quaternary ammonium compounds corresponding to formula (1)

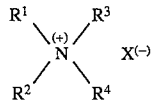

in which $R^1$, $R^2$ and $R^3$ are identical or different and are a linear or branched alkoxypolyoxyalkyl radical of the formula $(C_mH_{2m}O)_pR^5$, in which $R^5$ is hydrogen or a linear or branched alkyl radical having from 1 to 16 carbon atoms, m is an integer from 1 to 10 and p is a number from 1 to 15; or a linear or branched alkyl radical having from 1 to 30 carbon atoms; or an unsubstituted phenyl or naphthyl radical; or a substituted phenyl or naphthyl radical, with the substituents being halogen, $C_1$–$C_4$-alkyl, $C_1$–$C_4$-alkoxy, nitro or cyano;

$R^4$ is a linear or branched alkoxypolyoxyalkyl radical of the formula —$(C_mH_{2m}O)_pR^5$ in which m, p, and $R^5$ are as defined above; and $X^{(-)}$ is an inorganic anion; or the catalyst consists essentially of a mixture of component a) and a component b) which consists essentially of one or more quaternary ammonium salt(s) or phosphonium salt(s) of the formula (2)

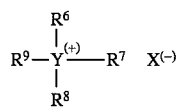

in which $R^6$, $R^7$, $R^8$ and $R^9$ are identical or different and are a linear or branched alkyl radical having from 1 to 22 carbon atoms; or an unsubstituted or substituted aryl radical or a $C_1$–$C_4$-alkylaryl radical, with aryl being phenyl or naphthyl and said substituents being halogen, $C_1$–$C_4$-alkyl, $C_1$–$C_4$-alkoxy, nitro or cyano; and Y is N or P; or the catalyst consists essentially of a mixture of component a) and a component c) which consists essentially of one or more polyether(s) of the formula (3)

in which $R^{10}$ and $R^{11}$ are identical or different and are hydrogen or a linear or branched alkyl radical having from 1 to 16 carbon atoms, x is an integer from 2 to 6 and r is a number from 0 to 20; or component c consists essentially of a crown ether; or the catalyst consists essentially of a mixture of components a), b) and c).

2. The process as claimed in claim 1, wherein the component a) makes up at least 5% by weight, preferably from 20 to 80% by weight, of the total catalyst.

3. The process as claimed in claim 1, wherein one or two alkoxypolyoxyalkyl radicals are present in the compound of the formula (1).

4. The process as claimed in claim 1, wherein two or three, preferably two, chlorine atoms in the compound of the formula (4) are replaced by fluorine atoms.

5. The process as claimed in claim 1, wherein the alkali metal fluoride is potassium fluoride, rubidium fluoride, cesium fluoride or a combination of these fluorides, in particular potassium fluoride.

6. The process as claimed in claim 1, wherein the molar ratio of catalyst to the compound of the formula (4) is equal to or less than 1:10, preferably from1:15 to 1:50.

7. The process as claimed in claim 1, wherein the reaction is carried out in the absence of a solvent.

8. The process as claimed in claim 1, wherein the reaction temperature is from 80° to 220° C., preferably from 90° to 180° C., in particular from 120° to 170° C.

9. The process as claimed in claim 1, wherein the compound of the formula (4) is 2,4-dichloronitrobenzene, 2,4-dichloro-3-fluoronitrobenzene, 2,4-dichloro-5-fluoronitrobenzene, 2,4,5-trichloronitrobenzene, 2,3,4-trichloronitrobenzene, 2,3,4-trichloro-5-fluoronitrobenzene or 2,4,5-trichloro-3-fluoronitrobenzene.

10. The process as claimed in claim 1, wherein the catalyst consists essentially of a component a) which consists essentially of one quaternary ammonium compound of the formula (1) or a plurality of quaternary ammonium compounds of the formula (1)

in which $R^1$, $R^2$, $R^3$ are identical or different and are a linear or branched alkoxypolyoxyalkyl radical of the formula —$(C_mH_{2m}O)_pR^5$, in which $R^5$ is hydrogen or a linear or branched alkyl radical having from 1 to 8 carbon atoms, m is an integer from 1 to 5 and p is a number from 2 to 10; or a linear or branched alkyl radical having from 1 to 18 carbon atoms; or an unsubstituted phenyl or naphthyl radical; or a substituted phenyl or naphthyl radical, with the substituents being halogen, $C_1$–$C_4$-alkyl, $C_1$–$C_4$-alkoxy, nitro or cyano;

$R^4$ is a linear or branched alkoxypolyoxyalkyl radical of the formula —$(C_mH_{2m}O)_pR^5$; and X is fluoride, chloride, bromide, $SO_4^{2-}/2$ or hydrogen sulfate; or the catalyst consists essentially of a mixture of component a) and a component b) which consists essentially of one quaternary ammonium salt or phosphonium salt of formula 2 or a plurality of quaternary ammonium salts or phosphonium salts of formula (2)

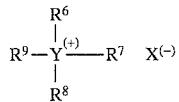
(2)

in which $R^6$, $R^7$, $R^8$ and $R^9$ are identical or different and are a linear or branched alkyl radical having from 1 to 16 carbon atoms; or an unsubstituted or substituted aryl radical or a $C_1$–$C_4$-alkyl-aryl radical, with aryl being phenyl or naphthyl and said substituents being halogen, $C_1$–$C_4$-alkyl, $C_1$–$C_4$-alkoxy, nitro or cyano; and Y is N or P; or the catalyst consists essentially of a mixture of component a) and a component c) which consists essentially of one polyether of the formula 3 or a plurality of polyethers of the formula (3)

$$R^{10}\text{—}(O\text{—}C_xH_{2x})_r\text{—}OR^{11} \quad (3)$$

in which $R^{10}$ and $R^{11}$ are identical or different and are hydrogen or a linear or branched alkyl radical having from 1 to 8 carbon atoms, x is the integer 2 or 3 and r is a number from 4 to 14; or component c consists essentially of a crown ether; or the catalyst consists essentially of a mixture of the components a), b) and c).

* * * * *